(12) United States Patent
Biedermann et al.

(10) Patent No.: US 12,329,372 B2
(45) Date of Patent: Jun. 17, 2025

(54) BONE ANCHOR ELEMENT FOR INSERTING INTO A BONE AND/OR FIXING TISSUE TO THE BONE, INSERTER, BONE ANCHOR SYSTEM AND METHOD FOR ASSEMBLING A BONE ANCHOR SYSTEM

(71) Applicant: KARL STORZ SE & Co. KG, Tuttlingen (DE)

(72) Inventors: Hannes Biedermann, Tuttlingen (DE); Daniel Fluri, Grenchen (CH); Nicolas Bouduban, Biel (CH)

(73) Assignee: KARL STORZ SE & Co. KG, Tuttlingen (DE)

( * ) Notice: Subject to any disclaimer, the term of this patent is extended or adjusted under 35 U.S.C. 154(b) by 363 days.

(21) Appl. No.: 17/192,468

(22) Filed: Mar. 4, 2021

(65) Prior Publication Data
US 2021/0290217 A1   Sep. 23, 2021

(30) Foreign Application Priority Data
Mar. 17, 2020   (DE) .................. 10 2020 107 245.7

(51) Int. Cl.
*A61B 17/04*   (2006.01)
*A61B 17/86*   (2006.01)
(Continued)

(52) U.S. Cl.
CPC ...... *A61B 17/0401* (2013.01); *A61B 17/0485* (2013.01); *A61F 2/0811* (2013.01);
(Continued)

(58) Field of Classification Search
CPC ........ A61B 17/0401; A61B 2017/0409; A61B 2017/0414; A61B 2017/0427;
(Continued)

(56) References Cited

U.S. PATENT DOCUMENTS 4,870,957 A * 10/1989 Goble ................. A61F 2/0811
623/13.12
5,156,616 A * 10/1992 Meadows ............ A61B 17/864
606/232
(Continued)

FOREIGN PATENT DOCUMENTS

CN      103370013 A  * 10/2013   ....... A61B 17/00491
DE      19505304 A1    9/1995
(Continued)

OTHER PUBLICATIONS

Savvidis, Givissis, Apostolou, Christodoulou, Is the Use of Bioabsorbable Materials in Orthopaedic Surgery Associated with Infections? Review of the Literature, Apr. 23, 2015, Inerntational Journal of Orthopaedics, vol. 2 No 2 (2015). http://www.ghrnet.org/index.php/ijo/article/view/843/1209 (Year: 2015).*

(Continued)

*Primary Examiner* — Ann Hu
(74) *Attorney, Agent, or Firm* — Jason H. Vick; Amped IP LLC

(57) ABSTRACT

A bone anchor element/inserter/system for inserting into a bone and/or fixing tissue to the bone. The bone anchor element has a proximal end, a proximal section, a distal section and a distal end, and the proximal section has on the outside a contoured. On the inside a continuous hollow space in the longitudinal direction there is a proximal opening and a distal opening. The distal section has in the longitudinal direction to the distal end a first transverse through-hole through the plate plane. A first transverse through-hole and a second transverse through-hole are separated by a web. The web has on its proximal side an abutment surface where when an eyelet is pushed through from the proximal opening through the continuous hollow space of the bone anchor element, through the distal opening (Continued)

Figure 1:
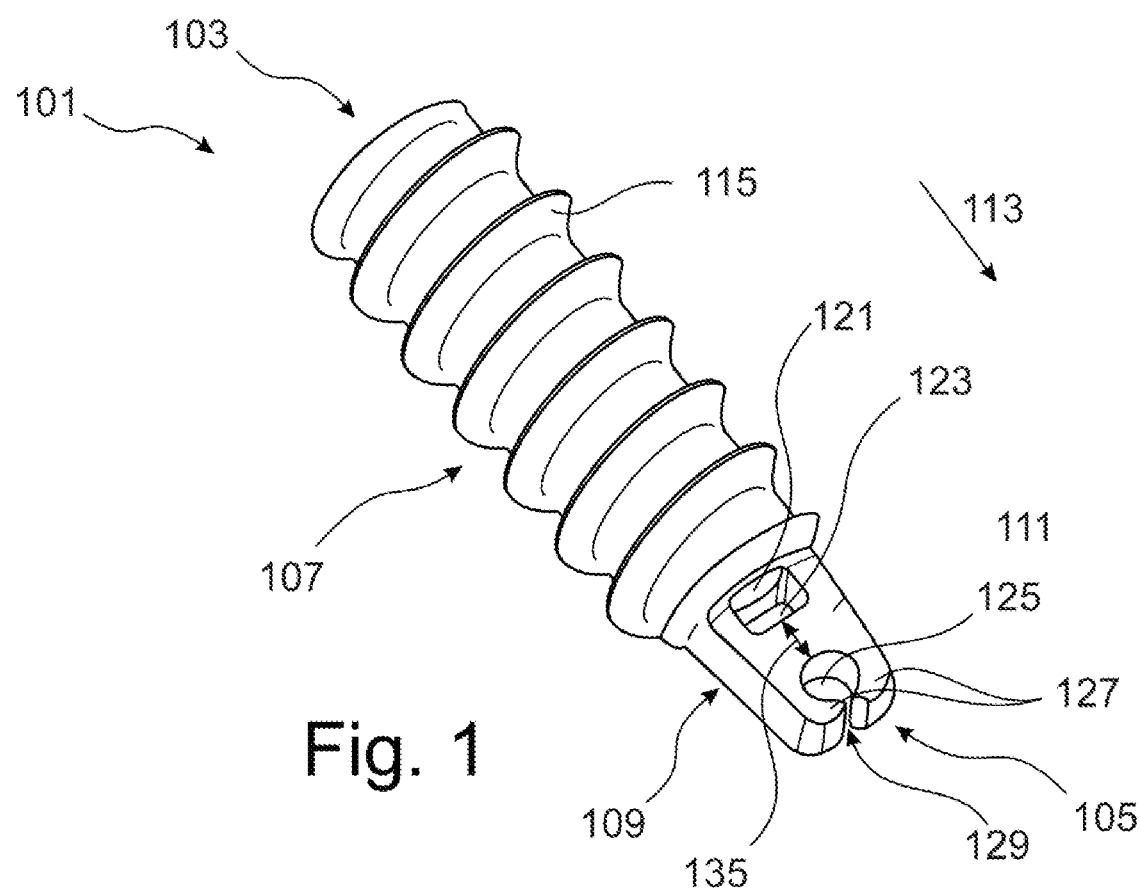

and through the first transverse through-hole in the longitudinal direction, the eyelet is guided outward.

21 Claims, 5 Drawing Sheets

(51) Int. Cl.
    *A61B 17/88*     (2006.01)
    *A61B 90/00*     (2016.01)
    *A61F 2/08*     (2006.01)

(52) U.S. Cl.
    CPC .............. *A61B 2017/0409* (2013.01); *A61B 2017/0414* (2013.01); *A61B 2017/044* (2013.01); *A61F 2002/0817* (2013.01); *A61F 2002/0852* (2013.01)

(58) Field of Classification Search
    CPC ...... A61B 2017/044; A61B 2017/0445; A61B 2017/0446; A61B 2017/0448; A61B 2017/045; A61F 2/081; A61F 2/0811; A61F 2002/0817; A61F 2002/0823; A61F 2002/0829; A61F 2002/0841; A61F 2002/0852; A61F 2002/0858; A61F 2002/0864; A61F 2002/087; A61F 2002/0876; A61F 2002/0882; A61F 2002/0888
    See application file for complete search history.

(56) References Cited

U.S. PATENT DOCUMENTS

| | | | | |
|---|---|---|---|---|
| 5,258,016 | A * | 11/1993 | DiPoto | A61B 90/06 606/232 |
| 5,466,243 | A | 11/1995 | Schmieding et al. | |
| 5,733,307 | A * | 3/1998 | Dinsdale | A61B 17/0401 606/232 |
| 6,610,079 | B1 * | 8/2003 | Li | A61B 17/068 606/76 |
| 7,682,374 | B2 * | 3/2010 | Foerster | A61B 17/0401 606/232 |
| 8,771,352 | B2 * | 7/2014 | Conner | A61F 2/0805 606/86 R |
| 8,882,801 | B2 * | 11/2014 | DiMatteo | A61B 17/0401 606/232 |
| 9,034,014 | B2 * | 5/2015 | Catania | A61B 17/0401 606/232 |
| 9,636,101 | B2 * | 5/2017 | Wolf | A61B 17/0401 |
| 9,706,987 | B2 * | 7/2017 | Cauldwell | A61B 17/06166 |
| 9,808,242 | B2 * | 11/2017 | Ng | A61B 17/1615 |
| 9,808,337 | B2 * | 11/2017 | Housman | A61B 17/0466 |
| 10,105,133 | B2 * | 10/2018 | Hester | A61B 17/0401 |
| 10,595,853 | B2 * | 3/2020 | Feezor | A61B 17/0485 |
| 10,888,363 | B2 * | 1/2021 | Greenhalgh | A61B 17/7098 |
| 10,993,712 | B2 * | 5/2021 | Lahteenkorva | A61B 17/0485 |
| 2006/0079904 | A1 | 4/2006 | Thal | |
| 2006/0293710 | A1 * | 12/2006 | Foerster | A61B 17/0401 606/232 |
| 2009/0076544 | A1 | 3/2009 | DiMatteo et al. | |
| 2010/0016905 | A1 * | 1/2010 | Greenhalgh | A61B 17/8875 606/313 |
| 2012/0022588 | A1 * | 1/2012 | Berg | A61B 17/8875 606/232 |
| 2012/0059416 | A1 * | 3/2012 | Justin | A61B 17/0401 606/232 |
| 2013/0267999 | A1 * | 10/2013 | Ng | A61B 17/1615 606/232 |
| 2016/0128685 | A1 * | 5/2016 | Hester | A61B 17/0401 606/232 |
| 2016/0192924 | A1 * | 7/2016 | Cauldwell | A61B 17/06166 606/232 |
| 2018/0338753 | A1 | 11/2018 | Housman | |
| 2019/0059874 | A1 * | 2/2019 | Rogers | A61B 17/0401 |
| 2019/0150912 | A1 | 5/2019 | Lahteenkorva et al. | |

FOREIGN PATENT DOCUMENTS

| | | | |
|---|---|---|---|
| DE | 202019005511 U1 * | 12/2020 | |
| EP | 0465910 A1 * | 1/1992 | ............ A61B 17/68 |
| EP | 1917915 A1 | 5/2008 | |
| EP | 2606833 A2 | 6/2013 | |
| WO | WO 2019/123462 | 6/2019 | |

OTHER PUBLICATIONS

European Search Report for corresponding European Application No. 21160387.3, mailed Aug. 2, 2021.

* cited by examiner

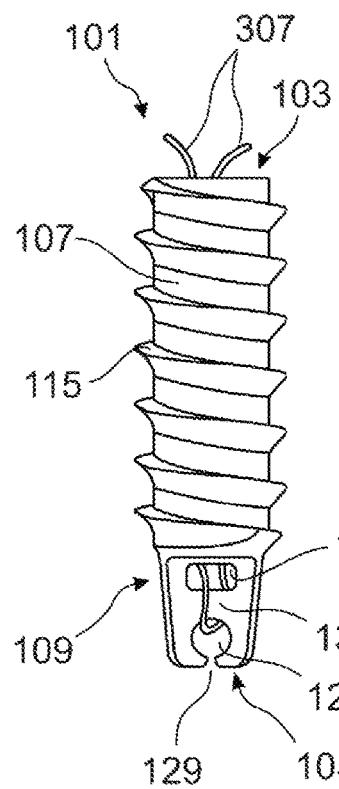
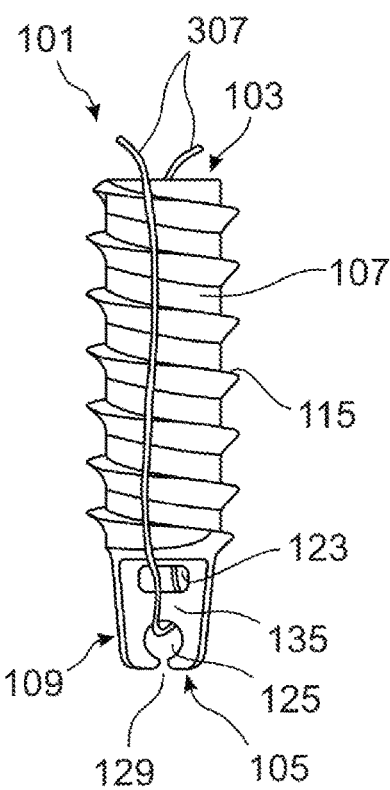
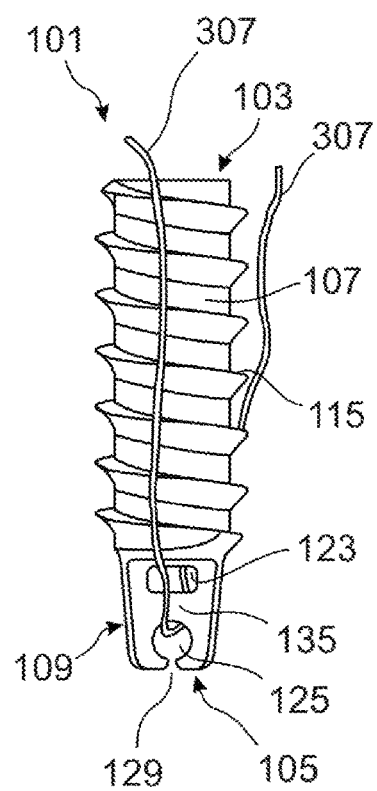
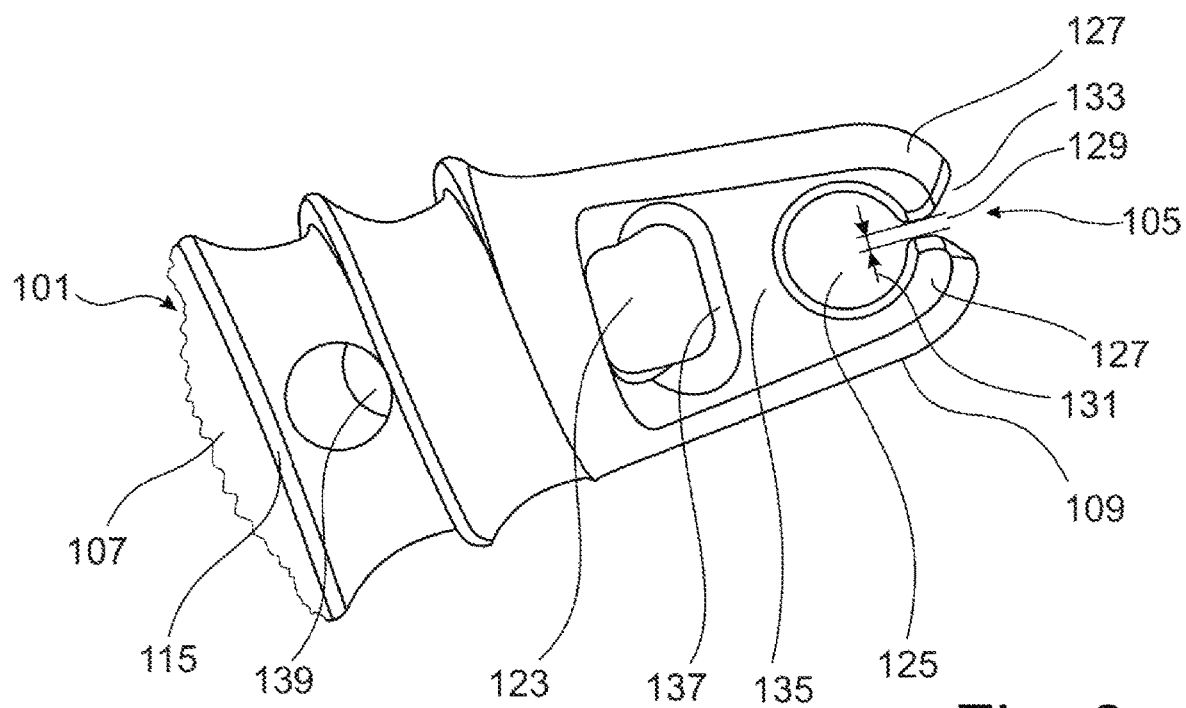

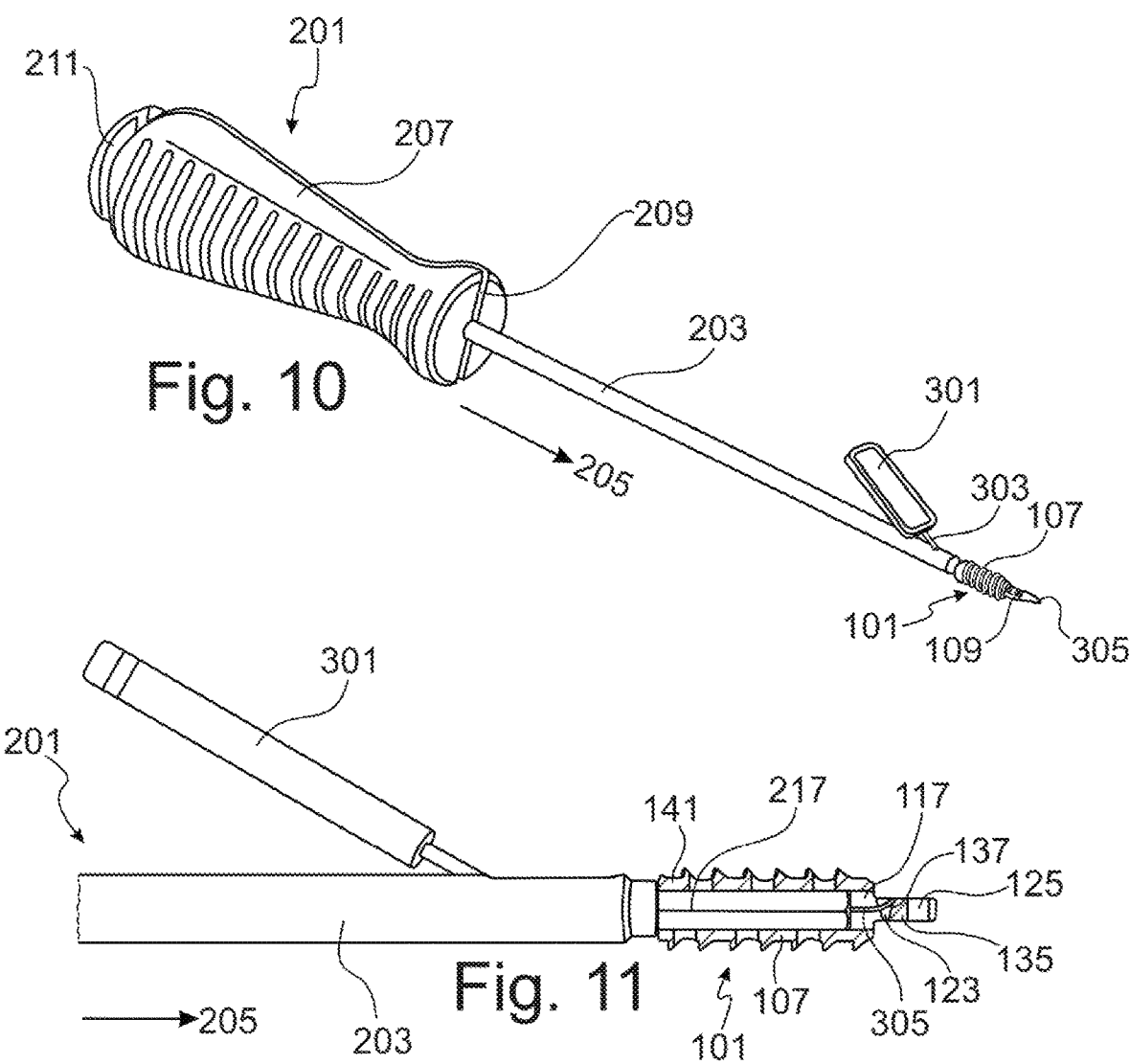
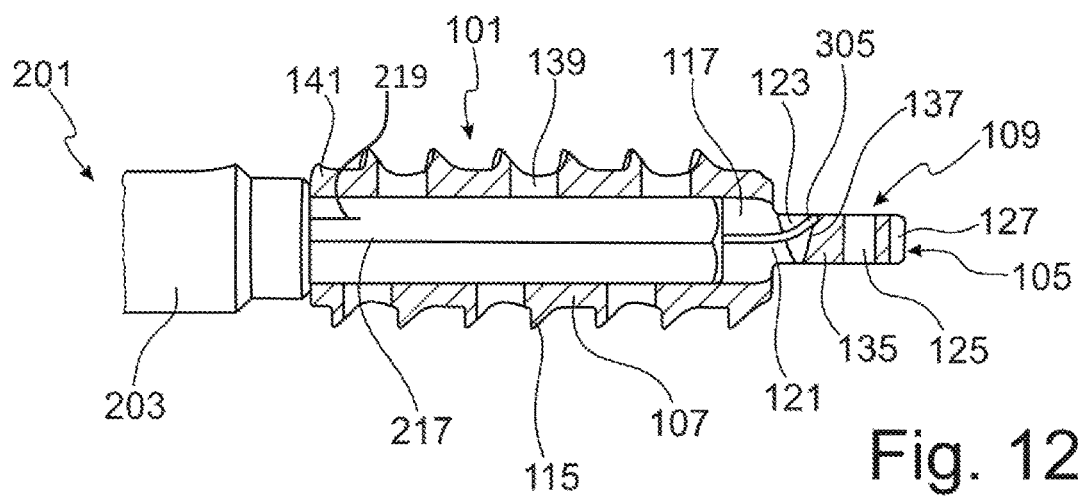

BONE ANCHOR ELEMENT FOR INSERTING INTO A BONE AND/OR FIXING TISSUE TO THE BONE, INSERTER, BONE ANCHOR SYSTEM AND METHOD FOR ASSEMBLING A BONE ANCHOR SYSTEM

CROSS-REFERENCE TO RELATED APPLICATIONS

This application claims the benefit under 35 U.S.C. 119 (a) to German Patent Application No. 10 2020 107 245.7, filed 17 Mar. 2020, the disclosure of which is incorporated herein by reference in its entirety.

The invention relates to a bone anchor element for inserting into a bone and/or fixing tissue to the bone, wherein the bone anchor element in a longitudinal direction has a proximal end, a proximal section, a distal section and a distal end, and the proximal section has on the outside a contoured projection for preventing a bone anchor element, which is inserted into the bone, from being pulled out and has on the inside a continuous hollow space in the longitudinal direction with a proximal opening and a distal opening, and the distal section is formed in a flattened, plate-shaped manner with a plate plane. Furthermore, the invention relates to an inserter for inserting a bone anchor element in a drill hole in a bone, a bone anchor system and a method for assembling a bone anchor system.

Bone anchor elements, also known as bone anchors, are deployed in the medical field to fix tissue that has detached from a bone, such as a torn tendon, back on to the bone. To do so, the bone anchor element typically has at least one hole or a holder for threading a thread, and the bone anchor element, loaded with the thread, is pushed or screwed into the bone. To this end, a so-called driving head or inserter is deployed, which is put on the proximal end of the bone anchor element.

Depending on the suturing method, the two thread ends of the thread held in the bone anchor element project out of the proximal end of the bone anchor element and are guided along the inserter and held. After driving in the bone anchor element and removing the driving head, the two free thread ends are deployed to attach the detached tissue to the bone by knotting the thread ends.

Alternatively, given a known knotless surgical technique, the thread is typically threaded through an opening in the bone anchor element, then one of the free thread ends is driven through the detached tissue using a needle and this thread end is then threaded again through the opening in the bone anchor element in the opposite direction. Consequently, the detached tissue is hereby fixed using a thread loop without a knot to the tissue, whereby the two suture ends are held on the bone anchor element. The bone anchor element is inserted into the bone and by pulling on the two free thread ends, the tissue to be fixed is pulled to the bone.

A system is known from US 2006/0079904 A1 for example having two bone anchors for repairing tissue, wherein the first bone anchor has on its proximal end a threading hole, through which a thread loop is passed. This first bone anchor is screwed into the bone, the thread loop is pulled through a detached tendon and then the thread loop end is accommodated inside a central opening on the distal end of the second bone anchor and the latter is inserted into the bone. The disadvantage here is that two bone anchors must be deployed and thus initially two drill holes must be made in the bone. In addition, the thread loop of the first bone anchor must be tied in the body to the second bone anchor by the surgeon.

US 2012/0022588 A1 also discloses a knotless method for attaching tissue to a bone, wherein a bone screw has a central bore for guiding onto an inserter rod and an anchor catches a thread loop, which is guided through the detached tissue. In addition, a second thread loop may be guided through the detached tissue; said loop is accommodated on its opposite thread loop end in an opening arranged on the distal end of the anchor and is attached by inserting the bone screw into the bone.

US 2016/0192924 A1 discloses a surgical suture anchor having an interior continuous hollow space and a recess connecting on the distal side, which is guided about a suture receiving element encircled by side walls about its distal tip for receiving two suture threads.

US 2009/0076544 A1 describes a suture anchor having a continuous hollow space and two through-holes formed as a recess separated by a suture receiving element, wherein the thread receiving element and the through-holes are encircled by side walls and the suture anchor has a tapering distal tip for insertion into a bone.

DE 195 304 A1 discloses a cannulated gripper having a distal-side hollow passage and on the proximal side a cap having a fluid barrier, wherein a screw-shaped thread anchor equipped with a thread passing through a terminal eye is inserted through the fluid barrier by means of the cannulated gripper using a rotating device.

WO 2019/123462 A1 discloses a medical implant having a plurality of reinforced, biodegradable fiber bundles, by means of which improved in-growth in a tissue is achieved by means of holes in the walls of the medical implant.

A disadvantage in known bone anchor elements and/or systems is that these are designed in a two- or multi-component manner and must first be assembled during the surgery by the surgeon. A further disadvantage is that the [thread] loading of the bone anchor system is predetermined and/or pre-assembled in known bone anchor systems and cannot be flexibly deployed or adjusted intraoperatively. In addition, the respective bone anchor often allows only one knotless or one conventional [thread] loading. Thus, there is no one bone anchor available which can be readily deployed for a variety of surgical techniques and for flexible loading with the suture thread.

The object of the invention is to improve prior art.

The task is achieved by a bone anchor element for insertion into a bone and/or fixing tissue to the bone, wherein the bone anchor element has in a longitudinal direction a proximal end, a proximal section, a distal section and a distal end, and the proximal section has on the outside a contoured projection for preventing the bone anchor element, which is inserted in the bone, from being pulled out, and on the inside a continuous hollow space in the longitudinal direction having a proximal opening and a distal opening, and the distal section is formed in a flattened, plate-shaped manner with a plate plane, wherein the distal section has in the longitudinal direction toward the distal end a first transverse through-hole through the plate plane, wherein the first transverse through-hole is connected to the continuous hollow space of the proximal section via the distal opening, and subsequently has a second transverse through-hole through the plate plane, wherein the first transverse through-hole and the second transverse through-hole are separated by a web of the plate-shaped distal section, and the second transverse through-hole has on the distal end a gap opening in the longitudinal direction and essentially transverse to the plate plane so that a suture material can be flexibly guided through the continuous hollow space, the first transverse through-hole, the second transverse through-hole and/or the gap opening, and the web has on its proximal side an inclined abutment surface at the first transverse through-hole in such a manner that in the event an eyelet is pushed from the proximal opening through the continuous hollow space of the bone anchor element, through the distal opening and through the first transverse through-hole in the longitudinal direction, the eyelet upon making contact with the inclined abutment surface is guided outward through the first transverse through-hole.

Consequently, the bone anchor element provides in particular a plurality of different thread-guiding possibilities, of which one or more that is or are particularly suited for a respective application, can be selected by a user during assembly and/or pre- or intraoperatively.

Thus, a bone anchor element is provided, which is conventionally preloaded with a thread as suture material and thus preassembled and/or which can be flexibly loaded before and/or during the surgery in a knotless manner. It is particularly advantageous that the bone anchor element and the thread guide can be optionally and/or flexibly deployed and/or adjusted intraoperatively. Consequently, the bone anchor element can be deployed in a versatile manner, and it is not necessary to prepare in advance two or more concepts for use and loading as well as for setting the suture during the surgery.

In addition, a preloading of the bone anchor element with a thread can be combined with an additional flexible loading of a thread or other threads during the surgery, so that two or more threads can be used with the bone anchor element. For example, the first transverse through-hole is hereby preloaded with a thread, while a thread can be taken up intraoperatively without a threading aid by means of the distal gap opening on the distal end of the bone anchor element and can be locked by inserting the bone anchor element into the bone. By means of the central gap opening on the distal end, the thread, guided through the second transverse through-hole, is encircled by two distal wings at the tip, which face each other at the gap opening and which prevent the thread from sliding out of the gap opening.

Thus, in a knotless surgical technique, the thread can be threaded through at least one of the transverse through-holes of the bone anchor element, after one of the free thread ends was pushed through the detached tissue using a needle system. Thereafter, this thread end is locked when the bone anchor element is inserted between the bone and the bone anchor element.

An essential idea of the invention is based in particular on providing a bone anchor element, which has on its distal section in the longitudinal direction two sequentially arranged transverse through-holes for receiving a thread or a plurality of threads, wherein each of the two through-holes can be flexibly preloaded manually or by means of a threading aid and/or loaded during the surgery. The web in the plate-shaped distal section between the two transverse through-holes hereby acts in particular as tension resistance and support for the two thread ends guided to the proximal end and/or due to its inclined abutment surface as a directed guideway for an eyelet or a thread. Thus, the thread may be guided as a loop around the web, wherein: either both thread ends are guided to the proximal end of the bone anchor element through the continuous hollow space of the proximal section; only one thread end is guided through the continuous hollow space and the other end is guided externally along the longitudinal direction of the proximal section to the proximal end; or both thread ends are guided externally along the longitudinal direction of the proximal section to the proximal end.

Thus, the bone anchor element allows for a conventional screw-in bone anchor concept, a push-in bone anchor concept, and a knotless bone anchor concept. The bone anchor is thereby not only deployable for fixing a tendon in the shoulder and hip region, but for a plurality of surgeries for fixing tendons and ligaments as well as labra, rotator cuff tears or torn capsules. For example, the bone anchor may have a maximum external diameter of 2.8 mm, 4.0 mm or 5.5 mm and a respective length of 8 mm, 15 mm or 18 mm. The ratio of the length of the distal section to the length of the proximal section is thereby in particular 0.54, 0.33 or 0.29.

By the design of the web, an eyelet of a threader, which is pushed lengthwise through the lateral proximal opening of the proximal section, the continuous hollow space and the distal opening into the first transverse through-hole, is always guided, due to the inclined abutment surface, on the distal section side predefined by the abutment surface, outward, particularly outward along an incline, to a side of the plate plane of the distal section. Thus, there is the user safeguard that the eyelet always exits outwardly on the same predefined side of the plate-shaped distal section of the bone anchor. This also prevents the eyelet and/or [thread] insertion aid from getting stuck in a longitudinal orientation in the first transverse through-hole.

Preferably, the abutment surface here is not formed over the entire height of the transverse through-hole transverse to the longitudinal direction of the bone anchor element, but begins for example only midway along the height of the transverse through-hole and is guided along the incline upward. To this end, the inclined abutment surface has for example an angle of 5° to 25°, preferably from 10° to 15°, relative to the transverse axis through the first through-hole, which is perpendicular to the longitudinal axis of the bone anchor element. The inclined abutment surface can hereby not only be formed on the proximal side of the web at the first through-hole, but also in the proximal direction on the interior sides of the distal section in the longitudinal direction around the first transverse through-hole. In particular, the inclined abutment surface inserted in the side walls of the proximal transverse through-hole can extend circumferentially in the longitudinal direction toward the proximal end of the bone anchor up to a point before the proximal end of the first transverse through-hole.

Advantageously and in particular, the gap opening on the distal end of the second transverse through-hole and the inclined abutment surface also enable subsequent [thread] loading. Thus, a suture material or a plurality of suture materials can be flexibly inserted and pass through different locations of the bone anchor element as needed, wherein loading with the suture material can take place manually as well as by means of an inserter and/or a threader in a flexible manner during pre-assembly and/or when using the bone anchor element.

The following terms shall be explained:

A "bone anchor element" (also referred to as a "bone anchor," "thread anchor," or "interference screw") is in particular an element for inserting into a bone and/or fixing tissue, particularly detached tissue, to the bone. Thus, a bone anchor is an implant for anatomical fixation. The bone anchor has in particular two transverse through-holes for threading a suture thread or a plurality of suture threads.

"Proximal" refers respectively to the end of an object, such as a bone anchor element or an inserter, which lies in a direction toward the body of the user and/or surgeon. Correspondingly, the end or the section, which lies on the side of the object away from the user of the object and consequently on the side of the bone and/or body to be operated on is referred to as "distal end" or "distal section", respectively. Thus, the distal end of the bone anchor element is inserted into the bone away from the surgeon.

"In the longitudinal direction" refers to the direction of the longest elongation and/or dimension of the bone anchor element. Thus, the longitudinal direction is also the direction in which the bone anchor element is inserted into a bone.

The "proximal section" (also referred to as "proximal body") has in particular a main body, wherein the main body is formed in the longitudinal direction as a hollow body and preferably as a hollow cylinder having a round cross-section. Obviously, the proximal section may also have an oval, triangular or polygonal cross-section. The proximal section has on its proximal end in particular a proximal opening, which borders in the interior the continuous hollow space, which is formed continuously up to a distal opening on the distal end of the proximal section. At the distal opening of the proximal section, the proximal section transitions into the distal section. The continuous bore of the proximal section may be formed as a continuous axial hole. However, this bore does not necessarily have to have a round cross-section, but may also have a polygonal, such as a hexagonal, shape in the cross-section. For example, a suture material can be threaded and/or an inserter can be inserted through the continuous hollow space of the proximal section.

The proximal section has in particular on its exterior side a contoured projection or a plurality of contoured projections. A "contoured projection" refers for example to a rib or a plurality of ribs. The rib or ribs may be arranged in a single-sided, circumferential and/or offset manner. The contoured projection may also be designed as a screw thread. A continuous screw thread pitch hereby preferably begins at the proximal end of the proximal section on the outside with a flat screw thread section and ends flush at the distal end of the proximal section also with a flat screw thread section. Depending on the design of the contoured projection, the bone anchor element can be anchored by screwing and/or pushing into the bone.

The proximal section transitions into the distal section at the distal end of the proximal section, wherein the distal section (also referred to as "distal tip") is formed in a flattened, plate-shaped manner having a plate plane and thus has, transverse to the plate plane in particular, a significantly lower height than the proximal section.

In the longitudinal direction following the distal opening of the proximal section, the first through-hole through the plate plane of the distal section is directly connected. Then, following in the longitudinal direction is a web and then the second transverse through-hole with a gap opening at the distal end of the distal section and thus at the distal end of the bone anchor element.

A "first transverse through-hole" and a "second transverse through-hole" (also known as a "loading hole"), refer in particular to a continuous opening and thus a hole transverse to the plate plane of the distal section.

A gap opening "essentially transverse to the plate plane" refers in particular to the fact that the gap opening goes completely through the plate plane, in such a manner that a thread can be threaded through the gap opening, arranged particularly in a vertical manner, into the second transverse through-hole. However, the gap opening does not have to be mandatorily perpendicular to the plate plane; instead, it may also be formed at an inclined angle to the plate plane. In this way, the gap opening can also pass through the plate plane at an angle.

"Eyelet" refers in particular to a wire and/or metal loop. An eyelet may also be in particular a loading wire bent into a loop, or also a suture thread bent into a loop. The eyelet is designed in particular as a loop at the end of a wire or suture thread, wherein the two wire ends or suture thread ends are held together by a threader, attached to a threader, or held together in another way, for example manually.

"Guided outward" refers in particular to the fact that the eyelet, upon contacting the inclined abutment surface through the first transverse through-hole, is guided out of the plate plane.

In another embodiment of the bone anchor element, the proximal section and/or the distal section tapers continuously or non-continuously from the respective proximal end to the respective distal end.

The insertion of the bone anchor element through a drill hole in the bone is thereby simplified and because of the tapering form of the distal section and/or the proximal section, the bone anchor element is optimally oriented and guided when being inserted inside the drill hole. In addition, the distal end and/or the distal section of the bone anchor element is thereby designed in a mechanically stable manner and withstands the forces during insertion.

A "drill hole" may also be in principle a push-in hole or a different type of hole made in the bone.

"Tapered" refers to the fact that the diameter of the proximal section and/or the distal section decreases from its respective proximal end in the longitudinal direction toward the respective distal end. The taper can hereby be formed both in the longitudinal direction as well as the transverse direction to the proximal section and/or to the distal section in a continuous or non-continuous manner, and thus be formed in a uniform or non-uniform manner.

To improve the mechanical stability of the bone anchor element, the first transverse through-hole through the plate plane is formed in an essentially quadrilateral, in particular rectangular, manner when viewed transversely to the longitudinal direction.

Thus, both the first transverse through-hole as well as the web connecting to the distal end in the longitudinal direction have sufficient mechanical stability opposing the forces during driving in of the bone anchor element. Thus, the bone anchor element may be inserted with the requisite pressure.

In addition, sufficient contact area and force transmission area is thereby provided on the bone anchor element for an inserter to insert the bone anchor element into the bore in the bone.

The first transverse through-hole is in particular deliberately devoid of a round cross-section, since with a round cross-section, the wall of the web between the first transverse through-hole and the second transverse through-hole would be formed with an excessively small material thickness, since for anatomical reasons, the length of the bone anchor element should be kept as minimal as possible in the longitudinal direction. By means of the quadrilateral form of the first through-hole, the web, with a corresponding material thickness, also offers a sufficient resistance to the tensile forces of the thread or threads.

In addition, the quadrilateral shape of the first transverse through-hole ensures that, in forming the contoured through-hole as a screw thread pitch, the last screw thread pitch is not damaged at the transition from the distal end of the proximal section to the distal section with the first transverse through-hole directly connecting after the distal opening.

To form the distal end of the distal section as two opposing clamping wings (clips) having a clamping tension at the gap opening, the second through-hole through the plate plane has an essentially round shape.

In this way, a thread can be gently inserted through the gap opening of the second transverse through-hole, wherein, due to the shape, which is determined by the second round transverse through-hole, of the remaining plate-shaped material at the distal end of the distal section around the gap opening and thus the formation of a clip, the thread material is however held securely in the second transverse through-hole by the compression of the gap opening by the clamping wings. In this way, by means of the gap opening, a thread can be received and then intraoperatively secured in the second transverse through-hole in a simple manner during a surgery without a threading aid, so that the suture thread is prevented from sliding outward through the gap opening.

"Essentially quadrilateral" in regard to the first transverse through-hole and "an essentially round shape" of the second transverse through-hole refer to the fact that the basic shape has the claimed shape, when viewed transversely to the plate plane. Thus, given an essentially quadrilateral shape, the first transverse through-hole may still have rounded corners for example to prevent wear or abrasion of the thread. Likewise, the essentially round shape of the second transverse through-hole does not necessarily have to be circular, but may also be formed in an oval manner, for example. Particularly for the bone anchor elements having an external diameter of 2.8 mm mentioned above for illustrative purposes, the first transverse through-hole may have an internal diameter of 0.8 mm (in the longitudinal direction)×1.0 mm (in the transverse direction) and the second transverse through-hole may have an internal diameter of 0.9 mm. For an external diameter of 4.0 mm, the first transverse through-hole measures 1.0 mm×1.6 mm and the second transverse through-hole measures 1.4 mm, and given an external diameter of 5.5 mm, the first transverse through-hole measures 1.1 mm×1.8 mm and the second transverse through-hole measures 1.4 mm.

In another embodiment of the bone anchor element, the distal end of the distal section is rounded about the gap opening in the plate plane and/or has after the gap opening a clearance space widening in the longitudinal direction to the distal end.

In this way, a thread to be inserted from the outside into the gap opening is threaded through the rounded portion gently without wear, and due to the clearance space widening in the longitudinal direction toward the gap opening until the distal end, and thus, when viewed from the opposite side in the direction of the proximal end, a clearance space narrowing to the gap opening, threading the thread through the gap opening into the second transverse through-hole is simplified. For example, the two clip wings may be rounded off in a convex manner around the gap opening.

Thus, the distal section in particular also has two rounded-off distal external corners, which allows thread-preserving threading as well as easier insertion of the bone anchor element into the bone.

In another embodiment of the bone anchor element, a gap width of the gap opening in the plate plane is adjusted to a diameter of the suture material.

The gap width can hereby specifically be adjusted only to the diameter of a suture material, or due to the interaction between the gap width and the encircling clip wings of the distal end of the distal section, the gap width can correspondingly induce a tension on the clip wings so that for example suture material with various diameters can be threaded through the gap opening and retained in the second transverse through-hole. The respective suture material is then hereby correspondingly threaded (clipped in) through the gap width of the gap opening with a correspondingly different force depending on its diameter.

In particular, the gap width of the gap opening is adjusted in such a manner that USP size 2 suture material can be threaded into the second transverse through-hole. To achieve this, the gap width may be 0.4 mm for example.

A "gap width" refers in particular to the dimension of the gap opening transverse to the longitudinal direction of the bone anchor element.

In another embodiment, the bone anchor element is designed as a single piece.

Accordingly, during the surgery, the bone anchor element does not have to be assembled from multiple parts or modified by the surgeon. In addition, the bone anchor element can be manufactured in a simple manner by means of injection molding. It is particularly advantageous that, with a single, one-piece bone anchor element, a plurality of loading options with one thread and a plurality of corresponding surgical techniques can be executed.

So that the bone anchor element can remain in the bone and thus in the human body, the bone anchor element consists of a biointegratable material.

Thus, after adhesion of the detached piece of tissue the bone anchor element can, with time, dissolve in the body, be broken down by the body and/or remain in the body in a bio-compatible manner. Preferably, the biointegratable material is completely replaced by bone material over the long term. In addition, using such a material prevents damage to the surrounding tissue and/or bone as well an interference in diagnostic imaging procedures.

A "biointegratable material" is in particular a biologically compatible material. Biointegratable material may be in particular a bioresorbable, biocompatible and/or a biodegradable material, for example a degradable polymer and/or a plastic. For example, the biointegratable material may consist of tricalcium phosphate. In contrast, PEEK is not degradable and yet has in particular the advantages of acceptance in surgical applications, mechanical stability, sterilizability and good manufacturability. Likewise, the biointegratable material may be a metal and/or a metal alloy.

To accelerate bone ingrowth into the bone anchor element and thus healing in the bone, the proximal section may have a perforation or a plurality of perforations.

In this way, the proximal section, formed as a hollow body, has one or more through-bores. Preferably, a plurality of perforations are formed offset to each other in a peripheral manner along the longitudinal direction.

To connect an inserter (also referred to as a driver) to the bone anchor element for inserting the bone anchor element into the drill hole in the bone, the proximal opening has an internal driving profile, particularly an internal hexagonal profile.

Thus, the necessary axial force and/or a torque can be applied to the inserter and transmitted via the internal driving profile to the bone anchor element for screwing and/or pushing into the bone.

The internal driving profile is formed in particular at the proximal opening in the direction of the longitudinal direction in the interior wall of the proximal section about the continuous hollow space. The internal driving profile may hereby also be formed in the initial region of the continuous hollow space or also be formed in the entire continuous hollow space up to the distal opening on the distal end of the proximal section so that the force transmitted by the inserter on the bone anchor element during insertion is improved. The length of the internal driving profile depends in particular on the length of the bone anchor element and the correspondingly deployed inserter.

In another embodiment of the bone anchor element, the bone anchor element has an anti-rotation protection element on its proximal end and/or at the proximal opening.

In this way, after attaching and/or connecting an inserter to and/or in the bone anchor element, rotation of the bone anchor element relative to the inserter is prevented, for example while the bone anchor element is screwed into the bone. In addition, it can thereby be ensured that the bone anchor element is connected to the inserter in a specifically oriented manner and thus, via the inclined abutment surface of the bone anchor element, the eyelet of a threader is always pushed upward or always pushed out on the same side of the distal section over the distal tip of the bone anchor element.

An "anti-rotation protection element" refers in particular to a structural component, which is designed in such a manner that it prevents the incorrect insertion and/or undesired rotation of the bone anchor element connected to the inserter. An anti-rotation protection element may involve for example a groove, into which a rib of the inserter engages or is clamped.

In another aspect of the invention, the task is achieved by an inserter for inserting a bone anchor element into a drill hole in a bone, wherein the inserter has a tool shaft in a longitudinal direction, and there is arranged a hand grip on a proximal end of the tool shaft, and a driving profile in an opposing distal end section for connecting to the bone anchor element, and the tool shaft has in at least one region before the distal end up to and including the driving profile a continuous hollow space in the longitudinal direction, wherein the tool shaft has before the distal end an insertion opening in the longitudinal direction, wherein the insertion opening is connected to the continuous hollow space, so that from the outside an eyelet can be pushed out through the insertion opening into the continuous hollow space and through the driving profile at the distal end.

Thus, an inserter is provided with which, after connecting the distal end of the inserter to the proximal section of the bone anchor element, a previously described bone anchor element can be inserted into a drill hole inside a bone and can be anchored there by pushing and/or screwing.

For the connection to the proximal section of the bone anchor element, the driving profile of the inserter is preferably pushed at the proximal end of the bone anchor element into the continuous hollow space of its proximal section. Depending on the length of the respective bone anchor element in the longitudinal direction, the driving profile of the inserter hereby engages at the end of the proximal section before the distal opening on the axial side and on the proximal side in the region of the proximal opening of the internal driving profile of the bone anchor element; the engagement occurs only at the end of the proximal section on the distal side and/or only at the end of the proximal section on the proximal side.

Preferably, the inserter is braced in the axial direction against the proximal side of the bone anchor element, against a shoulder on the distal end of the continuous hollow space, or on both. In particular, the inserter is braced in the axial direction against the distal side of the bone anchor element and/or is also clamped thereby. As a result, one single inserter can be used for all different sizes of bone anchor elements.

It is particularly advantageous that the inserter has an insertion opening, by means of which an eyelet of a threader can be intuitively pushed out forward over the distal end through the hollow space in the tool shaft of the inserter and the continuous hollow space of the connected bone anchor element. In addition, a threader is guided through and held by the insertion opening formed in the longitudinal direction in the tool shaft so that the threader cannot fall out. Furthermore, it is advantageous that the thread is hereby guided in a sterile environment through the inside of the bone anchor element and thus [through the inside] of the implant itself and protected.

Essentially, a thread, for example bent into a loop, can be threaded and guided directly without a threader through the insertion opening and the continuous hollow space of the inserter.

An "inserter" is in particular a tool for inserting a bone anchor into a drill hole in a bone. The inserter may already be pre-assembled with a thread or the thread is threaded after connecting the bone anchor element to the inserter. The inserter has in particular on the proximal end a hand grip, made of plastic for example, and a driving profile on the distal end. The tool shaft of the inserter is preferably electro-polished and passivated. The tool shaft is either formed entirely as a hollow shaft or it has a continuous hollow space in the longitudinal direction only at its forward distal end, wherein the hollow space connects to the insertion opening. The length of the tool shaft can be adjusted in particular to the intended use; thus, the tool shaft for a hip surgery is 80 mm longer for example than for a shoulder surgery. Likewise, the tool shaft may have a different diameter depending on the intended use. Preferably, the inserter can be used universally for various sizes of bone anchor elements.

"In a region before the distal end" refers in particular to proximally from the distal end.

An "insertion opening" (also known as "insertion window" or "slit") is in particular a recess in the longitudinal direction of the tool shaft in the region before the distal end, wherein the recess extends from the outside into the interior hollow shaft of the tool shaft. The insertion opening is preferably formed to be elongate in the longitudinal direction of the tool shaft. An insertion opening may also be a slit or a groove extending inward to the hollow space.

An eyelet of a threader or a wire loop is inserted into the insertion opening particularly from the outside and above in the direction from the proximal end of the inserter to the distal end of the inserter. Due to the fact that the eyelet can be pushed through the first transverse through-hole of the bone anchor element to the outside over the distal tip of the bone anchor element, a thread can be threaded through the eyelet and the thread can then be pulled through the gap opening in the second transverse through-hole against the distal side of the web. Then, a thread end is guided out of the bone anchor to its proximal end, while the other end is pulled out using the eyelet by retracting the threader through the distal opening of the continuous hollow space back via the proximal opening of the proximal section of the bone anchor. Thus, the inserter allows for the knotless preloading of the bone anchor using a threader or a [thread] loading wire.

In another embodiment of the inserter, the driving profile has an external driving profile, in particular an external hexagonal profile.

In this way, an optimal connection and force transmission of the inserter on an internal driving profile, particularly an internal hexagonal profile, of the bone anchor element can occur. The internal driving profile of the bone anchor element and the external driving profile of the inserter are hereby designed accordingly in a corresponding, interacting manner. Consequently, the inserter represents a hex drive for the bone anchor element.

To ensure a specified orientation of the bone anchor element on the distal end of the inserter and to prevent the connected bone anchor element from rotating, the inserter has in particular an anti-rotation protection element so that if the inserter is connected by means of the driver profile to a bone anchor element, a rotation of the connected bone anchor element is prevented.

In this way, it can be ensured that both the insertion opening in the tool shaft of the inserter as well as the exit of the eyelet upward through the first transverse through-hole lie on the top side of the inserter and the bone anchor, respectively.

An "anti-rotation protection element" 219 is essentially an anti-rotation protection element already defined above. To this end, preferably both the inserter as well as the proximal end of the bone anchor element each have a component, which interlocks with the other to form the anti-rotation protection. For example, the two corresponding anti-rotation protection elements are formed on the inserter and on the bone anchor element as plug and socket or as latch elements.

In another embodiment of the inserter, the hand grip has a recess and/or a spool for receiving a suture material.

In this way, the inserter can be provided in an already pre-assembled manner, loaded with a suture material. Likewise, after loading a bone anchor element with a thread, the two thread ends can be accommodated in the recess of the hand grip of the inserter and/or rolled up on its spool. Preferably, the thread ends are guided laterally on the grip in the longitudinal direction to the proximal end in a flush and snug manner. Obviously, the hand grip may also have a plurality of recesses in the longitudinal direction so that only one thread is guided into each recess. The spool for rolling up the excess thread material is preferably formed on the proximal end of the hand grip.

A "recess" is in particular a groove, which is formed in the external surface of the hand grip from the proximal to the distal end of the hand grip in the longitudinal direction.

In another aspect of the invention, the task is achieved by a bone anchor system having a previously described bone anchor element and a previously described inserter so that the inserter can be connected to the bone anchor element, a suture material can be flexibly threaded through the bone anchor element, and the bone anchor element can be inserted by means of the inserter into a drill hole in a bone.

Consequently, a pre-assembled bone anchor system is provided having a bone anchor element and inserter designed to correspond to and interact with each other.

In another embodiment of the bone anchor system, the bone anchor system is allocated a threader with an eyelet or the bone anchor system encompasses the threader with the eyelet, so that in the event of connecting the inserter to the bone anchor element, the eyelet of the threader can be pushed from the outside through the insertion opening into and through the hollow space of the tool shaft of the inserter through the continuous hollow space, the distal opening and the first transverse through-hole via the inclined abutment surface to the outside over the distal end of the bone anchor and a suture material can be threaded into the eyelet.

To provide a completely pre-assembled bone anchor system, the bone anchor system encompasses the suture material.

In an additional aspect of the invention, the task is achieved by a method for assembling a bone anchor system by means of a previously described bone anchor element and a previously described inserter or by means of a previously described bone anchor system, having the following steps:

Connecting the distal end of the inserter to the proximal end of the bone anchor element, Inserting an eyelet of a threader from the outside through the insertion opening into the hollow space of the tool shaft of the inserter, Pushing the eyelet through the hollow space of the tool shaft of the inserter and through the continuous hollow space, the distal opening and the first transverse through-hole via the inclined abutment surface to the outside over the distal end of the bone anchor element, Threading a suture thread of the suture material through the eyelet, Partially retracting the threader so that the eyelet is displaced toward the proximal end of the bone anchor element to the gap opening of the second transverse through-hole, Threading the suture thread into the gap opening of the second transverse through-hole, Further retracting the threader so that the suture thread contacts the distal side of the web, Pulling a first end of the suture thread out of the eyelet and guiding the first end along an exterior side of the bone anchor element and over its proximal end, Completely retracting the inserter from the insertion opening of the tool shaft so that a second end of the suture thread is pulled out of the insertion opening over the web, through the continuous hollow space of the proximal section and over the proximal end of the bone anchor element, and Securing or attaching the two ends of the suture thread to the hand grip of the inserter, so that the suture thread is attached in a knotless manner to the bone anchor element.

Additionally, prior to inserting the bone anchor element, a second suture thread can be threaded onto the bone anchor element using the previously described steps. Likewise, a suture thread can also be manually threaded through the gap opening of the second transverse through-hole and/or the first transverse through-hole can be loaded by means of a threader. Before the bone anchor is loaded with a suture thread or a plurality of suture threads as described above, the bone anchor may already have a preloaded suture thread, which is guided around the distal side of the web and both thread ends are pulled up through the continuous hollow space and over the proximal end.

In an elaboration of the method described above, after a bone anchor is loaded in the same or a different manner with a suture thread or with a plurality of suture threads, the task of assembling a bone anchor system can be solved additionally and separately by a method for inserting a bone anchor element in a bone and/or fixing tissue to the bone with the following additional step:

Inserting the bone anchor element by means of the inserter into a drill hole in the bone so that the bone anchor element is anchored in the bone and the suture thread is attached knotlessly to the bone anchor element.

Subsequently, the thread ends are used for suturing a detached tissue to the bone.

Thus, a method for assembling a bone anchor system is provided using the bone anchor element, in which in a versatile concept the bone anchor element can be conventionally loaded with a thread, loaded using a threader and/or manually loaded (knotlessly) during a surgery.

Figure 2:
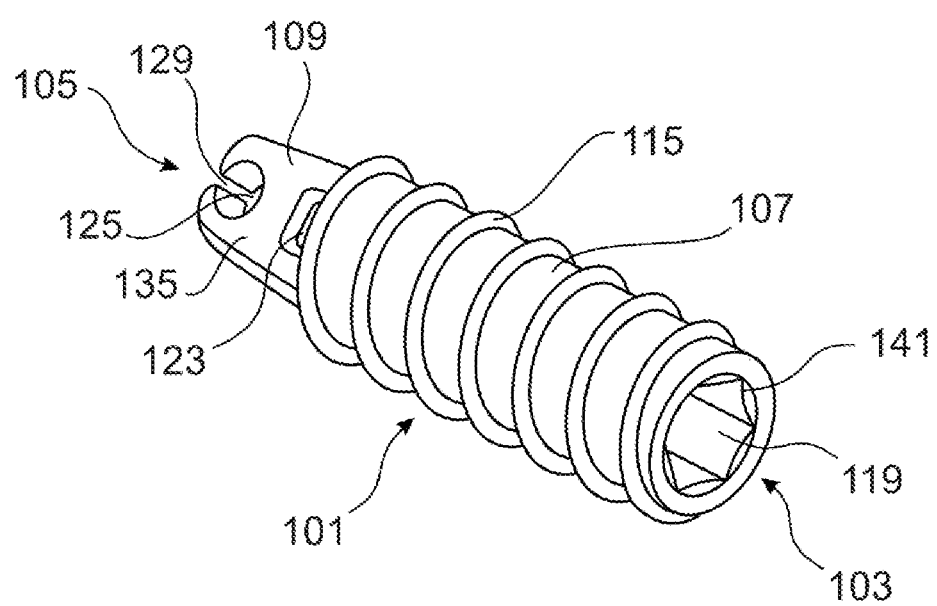
Figure 3:
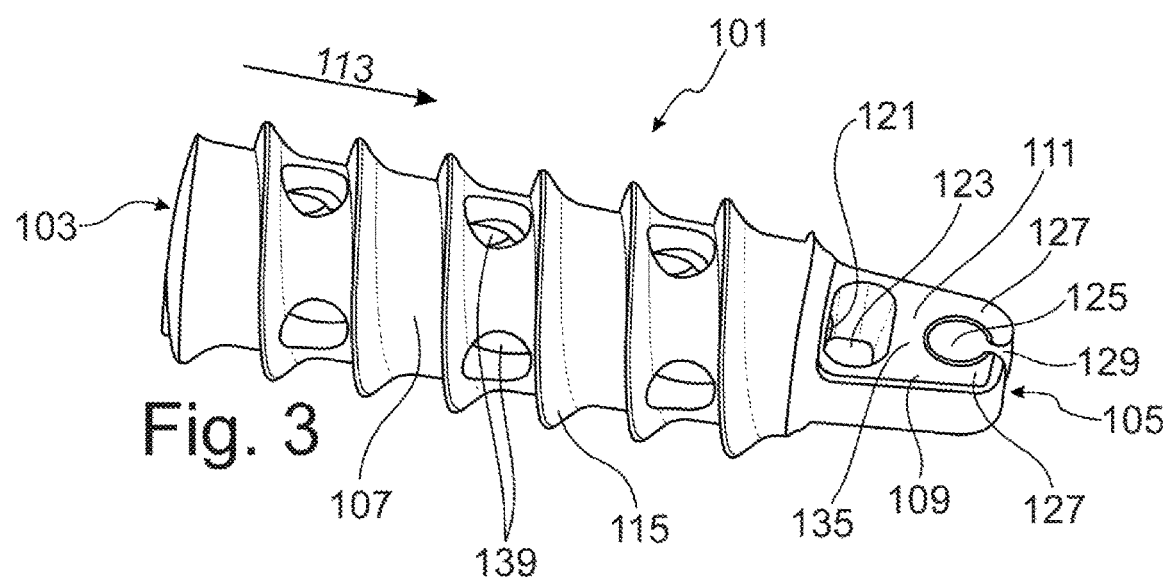
Figure 4:
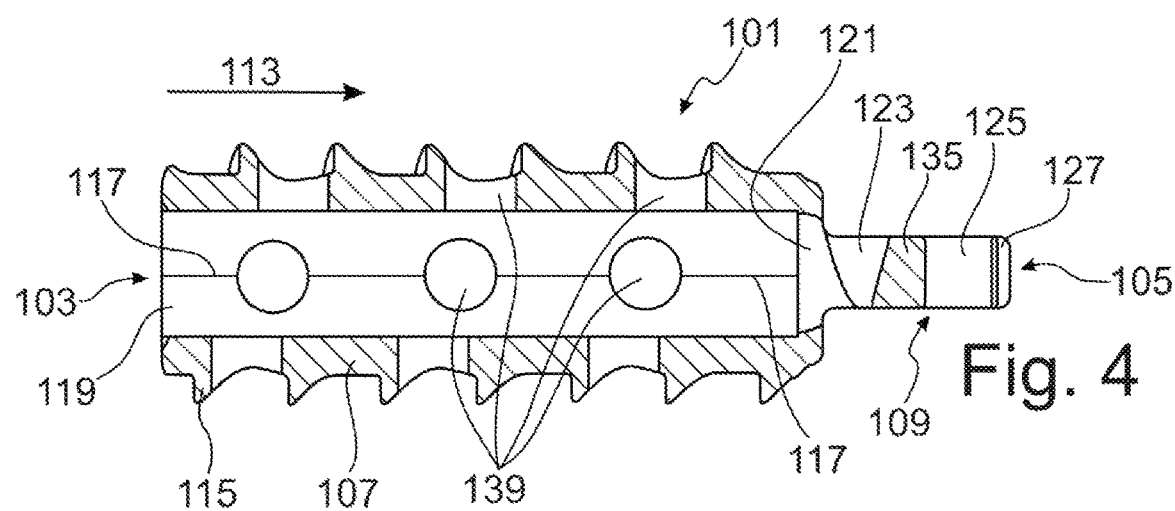
Figure 5:
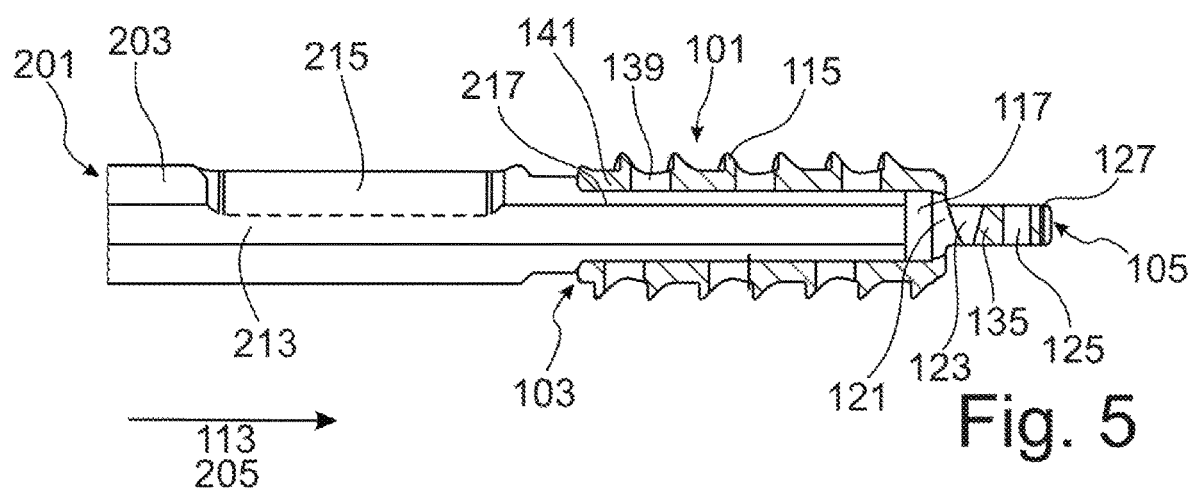
Figure 13:
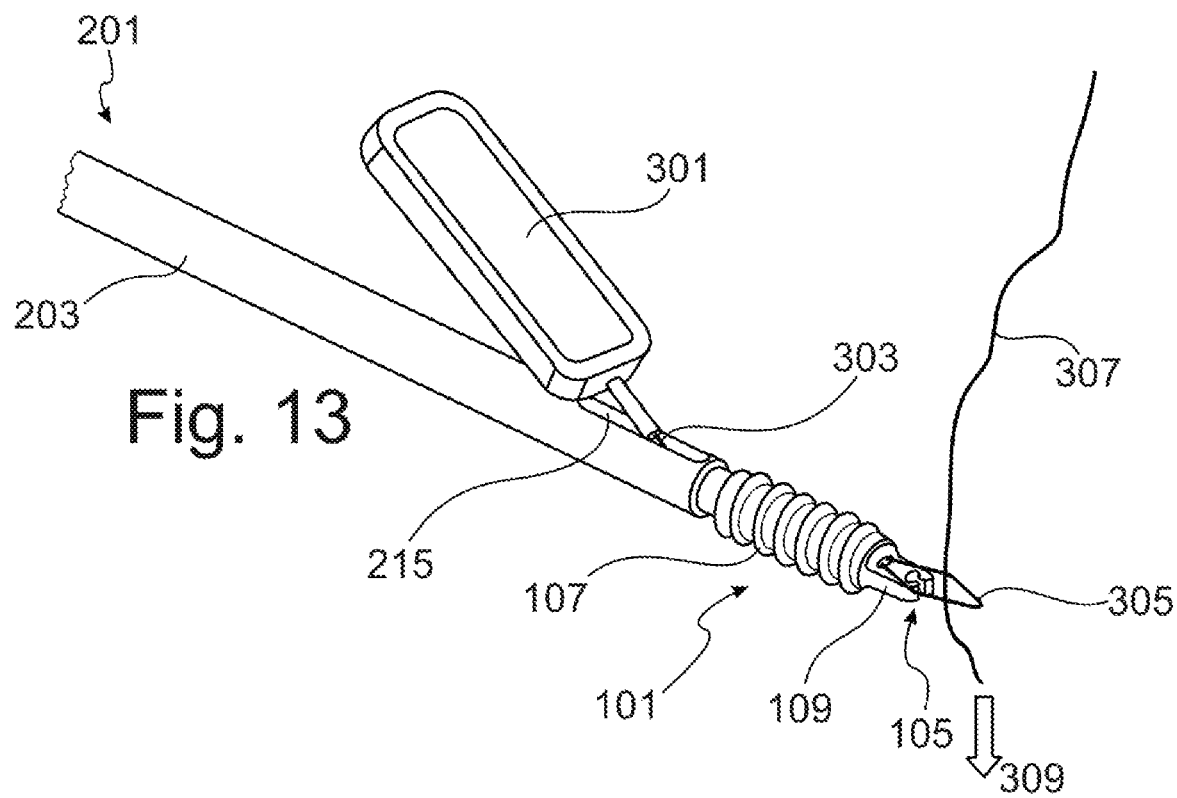
Figure 14:
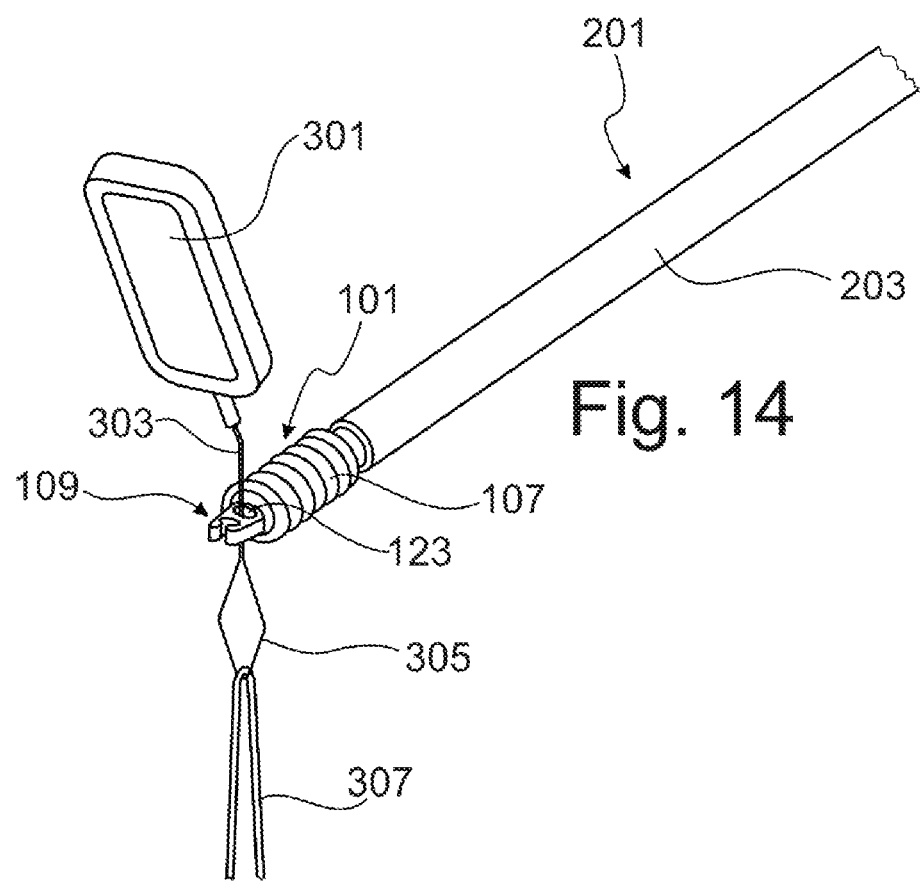

Hereinafter, the invention shall be explained in greater detail using embodiments. Depicted are:

FIG. 1 a perspective view of a bone screw looking at its distal end,

FIG. 2 a perspective view of the bone screw from FIG. 1 looking at its proximal end, FIG. 3 a perspective view of an alternative of the bone screw with perforations looking at the side, FIG. 4 a longitudinal section through the of the alternative bone screw from FIG. 3, FIG. 5 a longitudinal section through the alternative of the bone screw from FIGS. 3 and 4 with the inserted hollow shaft of an inserter, FIG. 6 an illustration of a conventional bone screw loaded with a thread, FIG. 7 an illustration of a bone screw knotlessly loaded using a threader, FIG. 8 an illustration of a bone screw loaded manually during a surgery, FIG. 9 a perspective view of the distal end of a bone screw with an inclined abutment surface of a first loading hole, FIG. 10 a perspective view of an inserter with a connected bone screw and inserted threader, FIG. 11 a partially perspective view and a partially sectional view as a detail from FIG. 10, FIG. 12 a magnified section of the bone screw from FIG. 11 with eyelet inserted, FIG. 13 a perspective view of a distal end of an inserter with connected bone screw, inserted threader and thread, FIG. 14 a perspective view of a distal end of an inserter with connected screw and inserted threader with thread at a first loading hole.

A bone screw 101 has a proximal end 103 and a distal end 105. In a longitudinal direction 113 of the bone screw 101, there is joined to the proximal end 103 a proximal body 107, which has internally a longitudinal bore 117. On the outside, a continuous screw thread 115 is guided along the proximal body 107, starting from the proximal end 103 to a distal opening 121 on the distal end of the longitudinal bore 117.

In the region of the distal opening 121, the proximal body 107 transitions to a distal tip 109 having a plate plane 111. In the longitudinal direction 113, joined to the distal opening 121 is a first loading hole 123, which runs transversely through the plate plane 111. The first loading hole 123 has a quadrilateral shape transverse to the longitudinal direction 113, wherein the corners of the square shape are rounded. A web 135 connects in the longitudinal direction 113 to the first loading hole 123. Following the web 135 in the longitudinal direction 113 is a second loading hole 125, which is formed as a round through-hole through the plate plane 111 and has on its distal end a gap opening 129.

The distal tip 109 tapers from the distal opening 121 to the distal end 105 of the bone screw 101 (see FIG. 1). Due to this tapering, the round shape of the second loading hole 125 and the gap opening 129, a clamping wing 127 is formed on each of the two sides of the second loading hole 125.

An internal hexagonal profile 141 is arranged on the proximal end 103 inside within the proximal opening 119 of the continuous longitudinal bore 117 (FIG. 2).

In an alternative of the bone screw 101 (FIGS. 3 and 4), the bone screw also has a plurality of perforations 139 extending through the proximal body 107, which are distributed at regularly spaced intervals over the cross-sectional surface and in the longitudinal direction 113 of the proximal body 107 (and thus the exterior surface), to improve later in-growth of a bone into the bone screw 101.

A hollow shaft 203 of an inserter 201 having an external hexagonal profile 217 on its distal end is inserted into the longitudinal bore 117 inside the bone screw 101. Accordingly, the hollow shaft 203 has a longitudinal direction 205, which coincides with the longitudinal direction 113 of the bone screw 101. The external hexagonal profile 210 is in contact on the inside with the walls of the longitudinal bore 117 of the bone screw 101. A shoulder of the hollow shaft 203 is in contact with the proximal end 103 of said screw.

Furthermore, the hollow shaft 203 of the inserter 201 has a slit 215, which is arranged before the external hexagonal profile 217 and is connected to the hollow space 213 (see FIG. 5).

Furthermore, in this alternative of the bone screw 101, the first loading hole is expanded upward (as shown in FIG. 4) in an approximately conical manner transverse to the longitudinal direction 112. By means of a non-depicted threading aid, a wire loop of the threading aid is pushed from the outside through the slit 215 and the hollow space 213 of the hollow shaft 203 in the longitudinal direction 205 to the distal opening 121. Due to the approximately cone-shaped, upwardly expanding form of the first loading hole 123 transverse to the longitudinal directions 205 and 113, the wire loop is guided upward to the outside through the upper opening of the first loading hole 123 so that said loop lies over the top side of the web 135 (not depicted in FIG. 5). Subsequently, a non-depicted suture thread can be threaded through this wire loop.

The bone screw 101 may be loaded with a thread 307 in different ways. For conventional loading, the thread 307 is guided through the gap opening 129 around the distal end of the web 135 and its side walls and the two thread ends go through the longitudinal bore 117 inside the proximal body 107 and the proximal opening 119 on the proximal end 103 of the bone screw to the outside (see FIG. 6).

For the knotless loading of the bone screw 101 using a threader, the thread is also guided through the second loading hole 125 around the distal side of the web 135, wherein a thread end is guided on the outside over the screw thread 115 to the proximal end 103 of the bone screw 101 and the other thread end is pulled through the longitudinal bore 117 inside the bone screw 101 to the proximal end 103 (see FIG. 7).

In a third knotless loading option, the thread 307 is manually threaded by the surgeon through the gap opening 129 into the second loading hole 125 and again lies around the distal end of the web 135. The two ends of the thread 307 are pulled up on the outside over the screw thread 117 to the proximal end 103 (see FIG. 8).

All three loading variants of the bone screw 101 depicted in FIGS. 6 to 8 having one or a plurality of threads can be combined with each other as desired.

In an alternative of the bone screw 101 having perforations 139, the first loading hole 123 has an inclined abutment surface 137 on the distal end of the first loading hole 123, wherein the inclined abutment surface 137 is formed in a tapering manner on both sides in the direction of the proximal end 103 (see FIG. 9). The inclined abutment surface 137 begins midway along the height of the distal-side wall around the first loading hole 123 and has a gradient of 10° or 15°. By means of this inclined abutment surface 137, an eyelet pushed through the longitudinal bore 117 of the proximal body 107 and through the distal opening 121 longitudinally into the first loading hole 123 is deflected and guided upward and out over the web 135.

Furthermore, FIG. 9 depicts in a magnified manner the distal end 105 of the distal tip 109. The gap opening 129 has a gap width 131. In the longitudinal direction 113 to the distal end 105, the gap opening 129 with the constant gap width 131 is followed by a conically opening clearance space 133, so that on both sides of the second loading hole 125 and the gap opening 129 two clamping wings 127 are formed. The gap width 131 of the gap opening 129 is hereby selected in such a manner that a thread guided by hand or by means of a threading aid from the outside, when subjected to a force, can be pushed through the conical clearance space 133 into the second loading hole 125.

A bone anchor system consists of an inserter 201 and a bone screw 101 (FIG. 10). The inserter 201 has a hand grip 207. In the top and bottom of the hand grip, a groove 209 in each case is routed from the distal end of the hand grip to the proximal end of the hand grip 207. A thread spool 211 is arranged at the proximal end of the hand grip 207.

Furthermore, the inserter 201 has a hollow shaft 203, as the latter is already depicted in FIG. 5. Inserted through the slit 215 of the hollow shaft 203 is a threader 301 with a wire 303 and a terminal eyelet 305, wherein the wire 303 and the eyelet 305 are guided through the hollow space 213 of the hollow shaft 203 and through the longitudinal bore 117 of the bone screw 101 so that the eyelet 305 is pushed out over the distal end 105 of the distal tip 109 (see FIG. 10).

Due to the inclined abutment surface 137 of the first loading hole 123, the eyelet 305 is deflected upward through the first loading hole 123 (FIGS. 11 and 12 show the state of the eyelet 305 just contacting the inclined abutment surface 137).

As depicted particularly in FIG. 13, the eyelet 305 is thereby pushed through on the top side of the distal tip 109 beyond the distal end 105 and a thread 307 can be pulled through the eyelet 305 in a threading direction 309. Subsequently, the threader 301 is pulled out again from the slit 215 to such a distance that the eyelet 305 finds its way into the region of the first loading hole 123 with the gap opening 129 and the thread 307 is threaded through the gap opening 129 into the second loading hole 125. Thereupon, one proceeds onward as described above in regard to FIG. 7.

In an alternative, the wire 303 of a threader 301 having a eyelet 305 arranged on the end is pushed through the first loading hole 123, and a thread 307 is pushed through the eyelet, wherein the two thread ends are oriented opposite a direction of the threader 301. Subsequently, the threader 301 is pulled upward so far that the eyelet 305 with the thread ends is pulled out at the top through the first loading hole 123.

Thereupon, a thread end of the thread 307 is taken out of the eyelet 305 and the eyelet 305 is removed from the thread 307. Subsequently, these two thread ends of the thread 307 are guided on both sides of the bone screw 101 and the hollow shaft 203 of the inserter 201 to the proximal end of the inserter 201 at its hand grip 207 and attached there as described above. This manual loading of the first loading hole 123 represents an additional loading option to the loading options described above and depicted in FIGS. 6 to 8.

Thus, a bone screw 101 is provided, which on the basis of the design of the first loading hole 123 and the second loading hole 125 can be flexibly preloaded and also be loaded with a thread or a plurality of threads using various loading methods and concepts during a surgery so that a flexibly usable bone screw 101 is provided for fixing a detached tissue to a bone.

LIST OF REFERENCE NUMBERS

101 Bone screw
103 Proximal end
105 Distal end
107 Proximal body
109 Distal tip
111 Plate plane
113 Longitudinal direction
115 Screw thread
117 Longitudinal bore
119 Proximal opening
121 Distal opening
123 First loading hole
125 Second loading hole
127 Clamping wing
129 Gap opening
131 Gap width
133 Conical clearance space
135 Web
137 Inclined abutment surface
139 Perforation
141 Internal hexagonal profile
201 Inserter
203 Hollow shaft
205 Longitudinal direction
207 Hand grip
209 Groove
211 Thread spool
213 Hollow space
215 Slit
217 External hexagonal profile
301 Threader
303 Wire
305 Eyelet
307 Thread
309 Threading direction

The invention claimed is:

1. A bone anchor element configured for insertion into a bone and/or fixing tissue to the bone, wherein the bone anchor element comprises:
   in a longitudinal direction, a proximal end, a proximal section, a distal section and a distal end,
   wherein the proximal section has on an outside a contoured projection to prevent the bone anchor element when inserted into the bone from being pulled out, and, on an inside, a continuous hollow space in the longitudinal direction having a proximal opening and a distal opening,
   wherein the distal section is a flattened, plate-shape configuration having a plate plane, wherein the plate plane is monolithic and includes two, parallel surfaces that bound the plate plane on an exterior portion,
   wherein the distal section, in the longitudinal direction to the distal end, has a first transverse through-hole through the plate plane, wherein the first transverse through-hole is connected to the continuous hollow space of the proximal section via the distal opening, and a second transverse through-hole through the plate plane, wherein the first transverse through-hole and the second transverse through-hole are separated by a web of the plate-shaped distal section,
   wherein the second transverse through-hole has on the distal end a gap opening in the longitudinal direction and transverse to the plate plane and configured such that a suture material can be flexibly-guided through the continuous hollow space, the first transverse through-hole, the second transverse through-hole and/or the gap opening, and the web has on its proximal side in relation to the first transverse through-hole an inclined abutment surface extending to one of the two, parallel surfaces that bound the plate plane on the exterior portion, wherein the bone anchor element is configured so that when an eyelet is pushed through from the proximal opening through the continuous hollow space of the bone anchor element, through the distal opening and through the first transverse through-hole in the longitudinal direction, the eyelet is guided outward to one of the two, parallel surfaces upon contacting the inclined abutment surface through the first transverse through-hole.

2. The bone anchor element according to claim 1, wherein the proximal section and/or the distal section taper(s) continuously or non-continuously from the respective proximal end to the respective distal end.

3. The bone anchor element according to claim 1, wherein the first transverse through-hole through the plate plane is formed in a quadrilateral manner, or in a rectangular manner transverse to the longitudinal direction.

4. The bone anchor element according to claim 1, wherein the second transverse through-hole through the plate plane has a round shape.

5. The bone anchor element according to claim 1, wherein the distal end of the distal section is rounded about the gap opening in the plate plane and/or has after the gap opening a clearance space widening in the longitudinal direction to the distal end.

6. The bone anchor element according to claim 1, wherein a gap width of the gap opening in the plate plane is adjusted to a diameter of the suture material.

7. The bone anchor element according to claim 1, wherein the bone anchor element is one piece.

8. The bone anchor element according to claim 1, wherein the bone anchor element comprises a biointegratable material.

9. The bone anchor element according to claim 1, wherein the proximal section has a perforation or a plurality of perforations.

10. The bone anchor element according to claim 1, wherein the proximal opening has an internal driving profile, or an internal hexagonal profile.

11. The bone anchor element according to claim 1, wherein the bone anchor element has on its proximal end and/or at the proximal opening an anti-rotation protection element.

12. The bone anchor element according to claim 1, wherein the proximal section is cylindrical and the exterior includes a thread.

13. The bone anchor element according to claim 1, wherein the inclined abutment surface is present on three sides of the first transverse through-hole.

14. An inserter configured to insert a bone anchor element into a hole in a bone, wherein the bone anchor element comprises:

in a longitudinal direction, a proximal end, a proximal section, a distal section and a distal end, wherein the proximal section has on an outside a contoured projection configured to prevent the bone anchor element when inserted into the bone from being pulled out, and, on an inside, a continuous hollow space in the longitudinal direction having a proximal opening and a distal opening, wherein the distal section is a flattened, plate-shape configuration having a plate plane, wherein the plate plane is monolithic and includes two, parallel surfaces that bound the plate plane on an exterior portion, wherein the distal section, in the longitudinal direction to the distal end, has a first transverse through-hole through the plate plane, wherein the first transverse through-hole is connected to the continuous hollow space of the proximal section via the distal opening, and a second transverse through-hole through the plate plane, wherein the first transverse through-hole and the second transverse through-hole are separated by a web of the plate-shaped distal section, wherein the second transverse through-hole has on the distal end a gap opening in the longitudinal direction and transverse to the plate plane and configured such that a suture material can be guided through the continuous hollow space, one or more of the first transverse through-hole, the second transverse through-hole and the gap opening, and the web has on its proximal side in relation to the first transverse through-hole an inclined abutment surface extending to one of the two, parallel surfaces that bound the plate plane on an exterior portion, wherein the bone anchor element is configured so that when an eyelet is pushed through from the proximal opening through the continuous hollow space of the bone anchor element, through the distal opening and through the first transverse through-hole in the longitudinal direction, the eyelet is guided outward to one of the two, parallel surfaces upon contacting the inclined abutment surface through the first transverse through-hole, and the inserter comprises:

a tool shaft in a longitudinal direction of the inserter, a hand grip arranged at a proximal end of the tool shaft, and a driving profile, configured to connect to the bone anchor element, is arranged in an opposing distal end section, wherein the tool shaft has, in at least one region before the distal end up to and including the driving profile, a continuous hollow space in the longitudinal direction of the inserter, wherein the tool shaft has before the distal end an insertion opening in the longitudinal direction of the inserter, wherein the insertion opening is connected to the continuous hollow space of the inserter, wherein when the inserter is connected to the bone anchor element, an eyelet can be pushed from the outside through the insertion opening into the continuous hollow space of the inserter all the way through the driving profile on the distal end section of the inserter and through the continuous hollow space of the bone anchor element through the distal opening into the first transverse through-hole of the bone anchor element and via the inclined abutment surface outward over the distal end of the bone anchor element.

15. The inserter according to claim 14, wherein the driving profile has an external driving profile, or an external hexagonal profile.

16. The inserter according to claim 14, wherein the inserter has an anti-rotation protection element, so that in the event of connecting the inserter by the driving profile to the bone anchor element, rotation of the connected bone anchor element is prevented.

17. The inserter according to claim 14, wherein the hand grip has a recess and/or a spool configured to receive the suture material.

18. A bone anchor system comprising:
a bone anchor element, wherein the bone anchor element has, in a longitudinal direction,
a proximal end, a proximal section, a distal section and a distal end,
wherein the proximal section has on an outside a contoured projection configured to prevent the bone anchor element when inserted into a bone from being pulled out, and, on an inside, a continuous hollow space in the longitudinal direction having a proximal opening and a distal opening,
wherein the distal section is a flattened, plate-shape configuration having a plate plane, wherein the plate plane is monolithic and includes two, parallel surfaces that bound the plate plane on an exterior portion,
wherein the distal section, in the longitudinal direction to the distal end, has a first transverse through-hole through the plate plane, wherein the first transverse through-hole is connected to the continuous hollow space of the proximal section via the distal opening, and a second transverse through-hole through the plate plane, wherein the first transverse through-hole and the second transverse through-hole are separated by a web of the plate-shaped distal section,
wherein the second transverse through-hole has on the distal end a gap opening in the longitudinal direction and transverse to the plate plane ad configured such that a suture material can be flexibly guided through the continuous hollow space, the first transverse through-hole, the second transverse through-hole and/or the gap opening, and
the web has on its proximal side in relation to the first transverse through-hole an inclined abutment surface extending to one of the two, parallel surfaces that bound the plate plane on the exterior portion,
wherein the bone anchor element is configured so that when an eyelet is pushed through from the proximal opening through the continuous hollow space of the bone anchor element, through the distal opening and through the first transverse through-hole in the longitudinal direction, the eyelet is guided outward to one of the two parallel surfaces upon contacting the inclined abutment surface through the first transverse through-hole, and
an inserter, the inserter is configured to be connected to the bone anchor element, wherein the suture material can be flexibly-threaded through the bone anchor element, and the bone anchor element can be inserted by the inserter into a drill hole in the bone.

19. The bone anchor system according to claim 18, wherein the bone anchor system is allocated a threader having the eyelet, or the bone anchor system encompasses the threader with the eyelet, wherein when connecting the inserter to the bone anchor element, the eyelet of the threader can be pushed from the outside through an insertion opening into and through a hollow space of the tool shaft of the inserter, through the continuous hollow space, the distal opening and the first transverse through-hole via the inclined abutment surface to the outside over the distal end of the bone anchor element and the suture material can be threaded into the eyelet.

20. The bone anchor system according to claim 18, wherein the bone anchor system encompasses the suture material.

21. A method to assemble a bone anchor system comprising:
using a bone anchor element, wherein the bone anchor element has, in a longitudinal direction, a proximal end, a proximal section, a distal section and a distal end,
wherein the proximal section has on an outside a contoured projection to prevent the bone anchor element when inserted into the bone from being pulled out, and, on an inside, a continuous hollow space in the longitudinal direction having a proximal opening and a distal opening,
wherein the distal section is a flattened, plate-shape configuration having a plate plane, wherein the plate plane is monolithic and includes two, parallel surfaces that bound the plate plane on an exterior portion,
wherein the distal section, in the longitudinal direction to the distal end, has a first transverse through-hole through the plate plane, wherein the first transverse through-hole is connected to the continuous hollow space of the proximal section via the distal opening, and a second transverse through-hole through the plate plane, wherein the first transverse through-hole and the second transverse through-hole are separated by a web of the plate-shaped distal section,
wherein the second transverse through-hole has on the distal end a gap opening in the longitudinal direction and transverse to the plate plane and configured such that a suture material can be guided through the continuous hollow space, the first transverse through-hole, the second transverse through-hole and/or the gap opening, and the web has on its proximal side in relation to the first transverse through-hole an inclined abutment surface extending to one of the two, parallel surfaces that bound the plate plane on the exterior portion,
wherein the bone anchor element is configured such that when an eyelet is pushed through from the proximal opening through the continuous hollow space of the bone anchor element, through the distal opening and through the first transverse through-hole in the longitudinal direction, the eyelet is guided outward to one of the two, parallel surfaces upon contacting the inclined abutment surface through the first transverse through-hole, and
using an inserter comprising a tool shaft comprising:
connecting a distal end of the inserter to the proximal end of the bone anchor element,
inserting an eyelet of a threader from the outside through an insertion opening into a hollow space of the tool shaft of the inserter,
pushing the eyelet through the hollow space of the tool shaft of the inserter and through the continuous hollow space, the distal opening and the first transverse through-hole via the inclined abutment surface to the outside over the distal end of the bone anchor element,
threading a suture thread of the suture material through the eyelet,
partially retracting the threader so that the eyelet is displaced toward the proximal end of the bone anchor element to the gap opening of the second transverse through-hole,
threading the suture thread into the gap opening of the second transverse through-hole,
further retracting the threader so that the suture thread contacts the distal side of the web,
pulling a first end of the suture thread out of the eyelet and guiding the first end along an exterior side of the bone anchor element and over its proximal end, completely retracting the threader out of the insertion opening of the tool shaft so that a second end of the suture thread is pulled out of the insertion opening over the web and through the continuous hollow space of the proximal section and over the proximal end of the bone anchor element, and holding or attaching the two ends of the suture thread to a hand grip of the inserter, so that the suture thread is knotlessly attached to the bone anchor element.

\* \* \* \* \*